(12) United States Patent
Mennen

(10) Patent No.: US 7,534,883 B2
(45) Date of Patent: May 19, 2009

(54) PROCESS FOR THE PREPARATION OF MELAMINE

(75) Inventor: Johannes Henricus J. H. Mennen, Meijel (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 11/883,384

(22) PCT Filed: Jan. 31, 2006

(86) PCT No.: PCT/NL2006/000053

§ 371 (c)(1),
(2), (4) Date: Aug. 22, 2007

(87) PCT Pub. No.: WO2006/083165

PCT Pub. Date: Aug. 10, 2006

(65) Prior Publication Data

US 2008/0119650 A1 May 22, 2008

(30) Foreign Application Priority Data

Feb. 4, 2005 (EP) .................................. 05075293

(51) Int. Cl.
*C07D 251/60* (2006.01)
*B01D 3/00* (2006.01)
*B01J 10/00* (2006.01)

(52) U.S. Cl. ...................................... 544/201; 544/203
(58) Field of Classification Search ................. 544/201, 544/203
See application file for complete search history.

(56) References Cited

U.S. PATENT DOCUMENTS 6,835,834 B2 * 12/2004 De Wit et al. ............... 544/201

FOREIGN PATENT DOCUMENTS

| WO | WO-96/20933 A1 * | 7/1996 |
| WO | WO 02/14289 A1 | 2/2002 |
| WO | WO 03/066605 A1 | 8/2003 |
| WO | WO 2004/065878 A1 | 8/2004 |

OTHER PUBLICATIONS

International Search Report mailed May 2, 2006 in PCT/NL2006/000053.
Written Opinion mailed May 2, 2006 in PCT/NL2006/000053.

* cited by examiner

*Primary Examiner*—Venkataraman Balasubramanian
(74) *Attorney, Agent, or Firm*—Nixon & Vanderhye P.C.

(57) ABSTRACT

The invention is directed to a process for the preparation of melamine connected through a carbamate concentration unit, comprising a desorption column in which a gas stream, comprising ammonia, carbon dioxide and water is generated, with a process for the preparation of urea, comprising a heat exchanger wherein a urea containing stream is present, wherein the gas stream, comprising ammonia, carbon dioxide and water, is send to the heat exchanger, wherein heat is exchanged with the urea containing stream and the gas stream, comprising ammonia, carbon dioxide and water is cooled and at least partially condensed to obtain an ammonium carbamate solution that is send to the process for the preparation of urea.

7 Claims, 1 Drawing Sheet

PROCESS FOR THE PREPARATION OF MELAMINE

Figure 1:
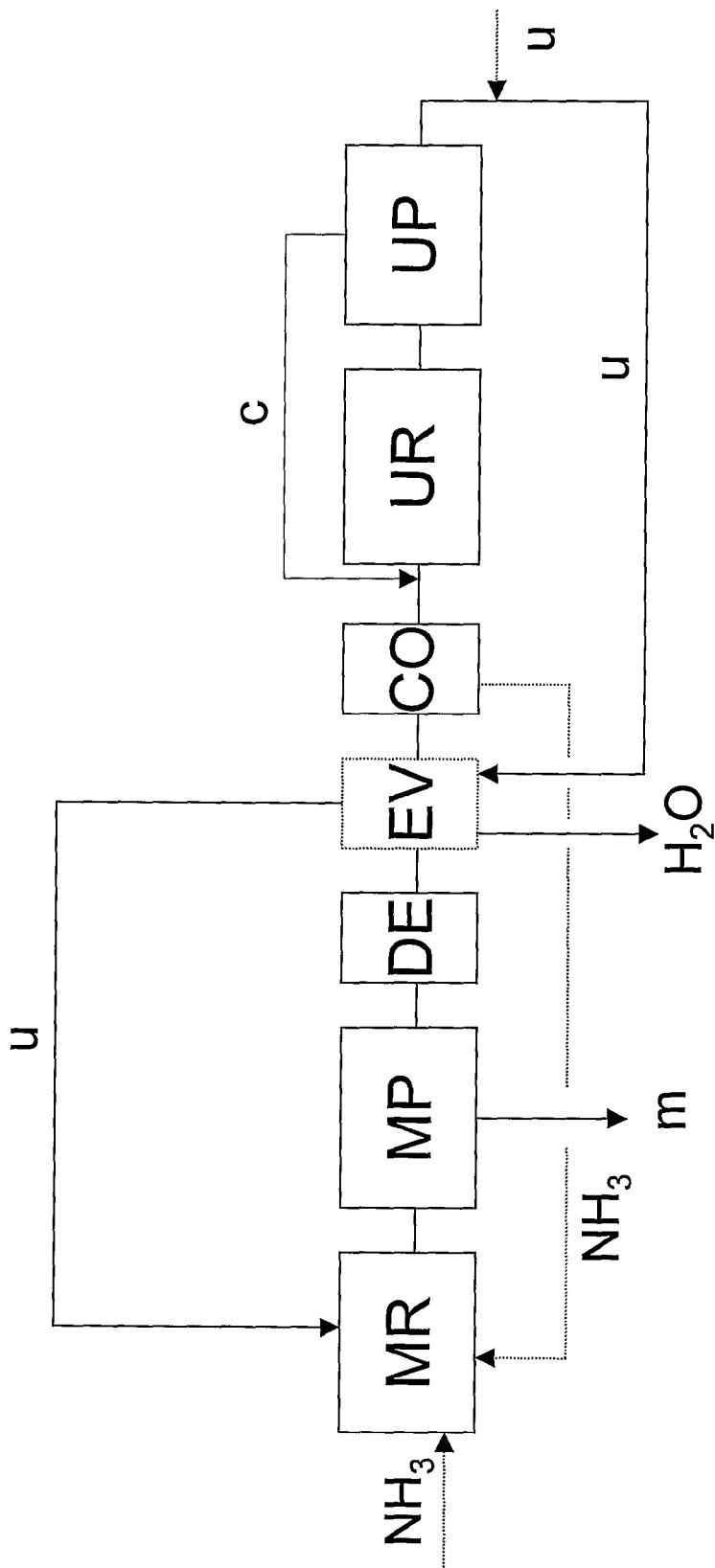

This application is the US national phase of international application PCT/NL2006/000053 filed 31 Jan. 2006 which designated the U.S. and claims benefit of EP 05075293.0, dated 4 Feb. 2005, the entire content of which is hereby incorporated by reference.

The invention is directed to a process for the preparation of melamine connected through a carbamate concentration unit, comprising a desorption column in which a gas stream, comprising ammonia, carbon dioxide and water is generated, with a process for the preparation of urea, comprising a heat exchanger wherein a urea containing stream is present.

Melamine is prepared using urea as the starting product. Not all the urea is converted to melamine and a stream comprising carbon dioxide, ammonia and water is formed as a by-product. This stream can be gaseous or be a solution of carbon dioxide and ammonia in water. A part of the carbon dioxide and ammonia in a solution is converted into ammonium carbamate. Carbon dioxide and ammonia can be used as starting products in a process for the production of urea. It is therefore common that a process for the preparation of melamine is connected with a process for the preparation of urea.

Because the stream comprising carbon dioxide and ammonia, comprises a lot of water and the presence of water during urea formation is detrimental to the conversion of carbon dioxide into urea this stream must be concentrated in a carbamate concentration unit before it is transferred to the process for the preparation of urea.

A carbamate concentration unit is defined as a unit wherein water is removed from a stream, comprising carbon dioxide, ammonia and water, originating from a process for the preparation of melamine. A carbamate concentration unit can comprise a desorber and/or a condenser and/or a gas/liquid separator.

The process for the preparation of urea can be a conventional urea process or a urea stripping process. A conventional urea comprises in the high-pressure part, normally, only a urea reactor. The urea solution formed in the urea reactor is lowered in pressure directly after the reactor and is further treated in a medium-pressure recirculation stage and thereafter in a low-pressure recirculation stage.

In a conventional urea plant the reactor is generally operated at a temperature of 180-250° C. and a pressure of 15-40 MPa. In a conventional urea plant ammonia and carbon dioxide are fed directly to the synthesis reactor. After expansion, dissociation and condensation in the medium-pressure urea recirculation stage, the raw materials that have not been converted into urea in a conventional urea plant are separated at a pressure between 1.5 and 10 MPa and returned as an ammonium carbamate stream to the urea synthesis. Subsequently in the low-pressure urea recirculation stage at a lower pressure of usually 0.1-0.8 MPa almost all the residual non-converted ammonia and carbon dioxide are removed from the urea synthesis solution, yielding a solution of urea in water. This solution of urea in water is then converted at reduced pressure in an evaporator into a concentrated urea melt.

A urea stripping plant comprises, in the high-pressure part of the plant, normally a reactor, a stripper, a condenser and optionally a scrubber.

In urea stripping plant the expulsion of the ammonia and carbon dioxide that have not been converted into urea for the major part takes place at a pressure that is virtually equal to the pressure in the reactor. In a urea stripping plant the reactor, the stripper and the condenser together usually form the high-pressure synthesis section.

The major part of the decomposition of non-converted ammonium carbamate and the expulsion of the excess ammonia takes place in a stripper, whether or not with a stripping gas being added. In a stripping process carbon dioxide and/or ammonia can be used as the stripping gas, before these components are fed to the reactor. It is also possible to apply "thermal stripping" here, which means that ammonium carbamate is decomposed exclusively by means of heat supply and the ammonia and carbon dioxide that are present are removed from the urea solution. Stripping can be carried out in one or more steps. A process is known for example in which first exclusively thermal stripping is carried out, after which a $CO_2$ stripping step takes place with more heat being supplied. The gas stream released from the stripper, which contains ammonia and carbon dioxide, is optionally returned to the reactor via a high-pressure condenser.

The synthesis reactor in a urea stripping plant is generally operated at a temperature of 160-240° C. and preferably at a temperature of 170-220° C. The pressure in the synthesis reactor is 12-21 MPa and preferably 12.5-19.5 MPa.

Downstream of the stripper the stripped urea synthesis solution is expanded to lower pressures in one or more pressure stages in the urea recirculation section and evaporated, with a concentrated urea melt being obtained and a low-pressure ammonium carbamate stream being returned to the high-pressure synthesis section. Depending on the process this ammonium carbamate can be recovered in a single process step or in several process steps operating at different pressures.

Conventional urea plants and urea stripping plants are, for instance, described in Ullmann's Encyclopedia of Industrial Chemistry, Vol. A 27, 1996, p. 339-350.

The process for the preparation of melamine can be a gas-phase process, but also a high-pressure process. A gas-phase process is a low-pressure process, in which the melamine reactor is operated at a pressure between 0.1 and 3 MPa. Melamine production processes are described for example in Ullmann's Encyclopaedia of Industrial Chemistry, Vol. A16, 1996, pp. 174-179.

A process for the preparation of melamine connected with a process for the preparation of urea is, for instance, described in U.S. Pat. No. 3,344,146. In this patent publication a process for the preparation of melamine is described that is connected with a process for the preparation of urea. Both processes are connected through a carbamate concentration unit comprising a desorber and at least one condenser. The urea process comprises a couple of heat exchangers. One of the heat exchangers is an evaporator wherein the urea solution is concentrated by evaporation of the water present in this solution to obtain a substantially water-free urea melt. The obtained urea melt is send to the process for the preparation of melamine.

After thorough investigations it has now been discovered that the amount of steam that is used in this process can be significantly reduced.

This is achieved by sending the gas stream, comprising ammonia, carbon dioxide and water obtained in the desorption column of the carbamate concentration unit to the heat exchanger in the process for the preparation of urea, wherein heat is exchanged with the urea containing stream and the gas stream, comprising ammonia, carbon dioxide and water is cooled and at least partially condensed to obtain an ammonium carbamate solution that is send to the process for the preparation of urea.

In this way the heat present in the gas stream, comprising ammonia, carbon dioxide and water is used to exchange heat with the urea containing stream present in the heat exchanger. In the process for the preparation of urea one or more heat exchangers can be present. The gas stream, comprising ammonia, carbon dioxide and water can be used in one or in all of the heat exchangers present.

The advantage is that the heat exchanger(s) do not have to be heated separately by steam, therewith saving steam and energy. The whole process can thus be operated at lower costs.

The ammonium carbamate solution that is obtained after condensation of the gaseous mixture comprising ammonia, carbon dioxide and water in the tubes of the evaporator can be directly returned to the process for the preparation of urea.

It can, for instance, being introduced in the high-pressure part of the process for the preparation of urea, or to one of the urea recirculation sections at lower pressure.

Preferably the ammonium carbamate solution is first treated in a condenser before it is sent to the process for the preparation of urea, to remove as much water as possible from the solution.

More preferably, the ammonium carbamate solution is sent to the urea reactor in the process for the preparation of urea.

The heat exchanger is preferably an evaporator in the process for the preparation of urea.

Preferably the ammonium carbamate solution is heated before it is send to the urea reactor. By heating the solution part of the ammonium carbamate decomposes into ammonia and carbon dioxide and a gas/liquid mixture is obtained.

By introduction of the gas/liquid mixture the conversion to urea in the urea reactor is much higher.

The invention is also directed to a plant for the preparation of melamine connected through a carbamate concentration unit, comprising a desorption column, with a process for the preparation of urea, comprising a heat exchanger. Such a plant is, for instance, described in U.S. Pat. No. 3,344,146, mentioned above.

It has now been discovered that when there is a line connecting the desorption column with the heat exchanger steam and energy can be saved and thus the plant can be operated at lower operation costs.

Preferably, the heat exchanger is an evaporator.

The process according to the invention is described in more detail in FIG. 1.

In FIG. 1 the various units of a plant for the preparation of melamine according to the invention are shown.

A melamine reaction zone (MR) is fed with urea (u) that is produced in the urea reaction zone (UR). The urea (u) is, after leaving the urea reaction zone (UR), purified in the urea purification zone (UP) and concentrated in the evaporator (EV). Optionally, also ammonia ($NH_3$) can be fed to the melamine reaction zone (MR). This ammonia can be fed from an external source or be recycled from a condenser (CO).

The melamine (m) that is produced is sent to a melamine purification zone (MP) wherein the melamine (m) is separated from the by-products. This by-products are, in the form of a carbamate-containing stream, sent to a carbamate concentration unit, comprising a desorption column (DE), wherein water is removed from the carbamate-containing stream. Thereafter the carbamate-containing stream is sent to a condenser and thereafter to a urea reaction unit (UR) wherein the carbamate is converted at high temperature and pressure into urea (u). Before the carbamate enters the condenser (CO) its heat is exchanged in an evaporator (EV) with the urea coming from the urea purification unit (UP). The carbamate-containing stream is cooled and the urea is heated in this evaporator (EV).

The urea that is formed in the urea reaction unit (UR) is sent to the urea purification unit (UP), wherein not converted carbamate is separated from the urea and recycled to the urea reaction unit (UR). If necessary urea from an external source can be added to the urea stream (u) that is sent to the evaporator (EV). In the evaporator (EV) the urea is heated and water is evaporated and removed.

The invention claimed is:

1. Process for the preparation of melamine which comprises a melamine preparation zone connected to a urea preparation zone through a carbamate concentration zone, wherein the process comprises:
    (a) generating a gas stream which is comprised of ammonia, carbon dioxide and water in a desorption column of the carbamate concentration zone,
    (b) generating a urea-containing stream in the urea preparation zone;
    (b) directing the gas stream and the urea-containing stream to a heat exchanger of the carbamate concentration zone, and
    (c) heat-exchanging the gas stream and the urea-containing stream in the heat exchanger of the carbamate concentration zone so that heat is exchanged between the urea-containing and the gas stream to thereby heat the urea-containing stream and to cool and at least partially condense the gas stream to obtain an ammonium carbamate solution therefrom, and
    (d) directing the ammonium carbamate solution from the heat exchanger to the urea preparation zone.

2. Process according to claim 1, further comprising treating the ammonium carbamate solution in a condenser upstream of the urea preparation zone.

3. Process according to claim 1, wherein the heat exchanger is an evaporator.

4. Process according to claim 1, wherein the urea preparation zone comprises a urea reactor, and wherein the process comprises directing the ammonium carbamate solution from the heat exchanger to the urea reactor.

5. Process according to claim 4, further comprising heating the ammonium carbamate solution before the ammonium carbamate solution is directed to the urea reactor in the urea preparation zone.

6. A process for the production of melamine comprising a melamine production zone, a urea production zone, and a carbamate concentration zone connecting the melamine and urea production zones, wherein the process comprises:
    (a) generating in the melamine production zone a melamine-containing stream and a gaseous by-product stream comprising carbon dioxide, ammonia and water,
    (b) generating a urea-containing stream in the urea production zone,
    (c) directing the by-product stream to a desorption column in the carbamate concentration zone to remove water from the by-product stream and form a carbamate-containing stream,
    (d) heat-exchanging the carbamate-containing stream and the urea-containing stream formed in the urea production zone in a heat exchanger upstream of the urea production zone so as to cool the carbamate-containing stream and heat the urea-containing stream,
    (e) directing the cooled carbamate-containing stream from the heat exchanger to the urea production zone, and (f) directing the heated urea-containing stream from the heat exchanger to the melamine production zone.

7. The process of claim 6, wherein the heat exchanger is an evaporator, and wherein the urea-containing stream is concentrated in the evaporator by removal of water therefrom, the concentrated and heated urea-containing stream then being directed to the melamine production zone.

* * * * *